United States Patent [19]

Wolfe et al.

[11] Patent Number: 4,543,098
[45] Date of Patent: Sep. 24, 1985

[54] TAMPON WITH RESILIENT COMPONENT AND MICROFIBER INSERT

[75] Inventors: Dexter L. Wolfe; Robert J. Peerenboom, both of Outgamie County, Wis.

[73] Assignee: Kimberly-Clark Corporation, Neenah, Wis.

[21] Appl. No.: 663,637

[22] Filed: Nov. 29, 1984

Related U.S. Application Data

[63] Continuation of Ser. No. 452,644, Dec. 23, 1982, abandoned.

[51] Int. Cl.⁴ ............................................. A61F 13/16
[52] U.S. Cl. ................................... 604/370; 604/904
[58] Field of Search ............... 604/904, 370, 380, 382, 604/383, 371, 372, 378

[56] References Cited

U.S. PATENT DOCUMENTS

| | | | |
|---|---|---|---|
| 3,340,874 | 9/1967 | Burgeni | 604/904 |
| 3,886,942 | 6/1975 | Bernardin | 604/370 |
| 3,976,075 | 8/1976 | Chinai et al. | 604/382 |
| 3,994,298 | 11/1976 | Des Marais | 604/904 |
| 4,274,412 | 6/1981 | Austin | 604/904 |
| 4,327,728 | 5/1982 | Elias | 604/904 |
| 4,335,722 | 6/1982 | Jackson | 604/904 |
| 4,341,214 | 7/1982 | Fries et al. | 604/904 |
| 4,397,644 | 8/1983 | Matthews et al. | 604/370 |

*Primary Examiner*—John D. Yasko

[57] ABSTRACT

A tampon is provided with a pledget having an outer layer having a web of thermoplastic fibers or mixtures thereof which is integrated to a nonwoven thermoplastic cover. The pledget also includes an absorbent insert which may be a thermoplastic nonwoven microfibrous web.

6 Claims, 4 Drawing Figures

TAMPON WITH RESILIENT COMPONENT AND MICROFIBER INSERT

This is a continuation of co-pending application Ser. No. 452,644 filed on Dec. 23, 1982, now abandoned.

FIELD OF THE INVENTION

This invention relates to a tampon and particularly a resilient shape conforming tampon.

BACKGROUND OF THE INVENTION

Tampon pledgets have been traditionally made from cellulose or cellulose derived materials such as rayon. These pledgets have been formed in a bulky rectangular web and compressed in some manner to form a cylinder of reduced bulk. Compression is utilized to add absorbency per unit volume to the pledget.

Cellulosic materials, while they are relatively inexpensive and are effective absorbents, do suffer from some disadvantages. Compressed pledgets are relatively inflexible and rigid and are therefore uncomfortable during insertion. While compression maximizes the amount of material available for absorption per unit volume for the cellulose type absorbent, the material must re-swell to fully utilize its absorbent capacity. Complete re-swelling, however, seldom occurs.

Attempts have been made to produce tampons having deformable and resilient pledgets with good absorbent capacity. An example of such a tampon was the RELY tampon sold by Procter & Gamble. In this particular tampon a compressible resilient foam was combined in discrete chunks with very finely divided superabsorbent material. While this tampon did produce excellent absorbent capacity and component, this tampon has been linked to toxic shock syndrome and has been withdrawn from the market place. Several other attempts have been made to utilize hydrophilic foam such as disclosed in British Pat. No. 1,595,139. Hydrophilic foams, however, suffer from the disadvantage that when they are compressed the fluid entrapped within is liberated much like wringing a wet sponge.

Other tampons have been made which are designed to be soft and flexible but are usually found to be either difficult to manufacture or lacking in absorbency. U.S. Pat. No. 3,857,395 which discloses a drapable covered absorbent batt useful as a tampon pledget is an example of typical art in this area.

SUMMARY OF THE INVENTION

According to this invention a tampon is provided with a two component pledget characterized by resilience, ease of compression and high levels of absorbency without using technology for fluid transfer and for the relationship of the individual elements of certain of the components is described in U.S. Pat. No. 4,397,644 issued to Matthews et al. foams or an exposed superabsorbent material. The outer or transfer layer of the pledget is made from a web having thermoplastic fibers which is integrated with a nonwoven thermoplastic fibrous cover. (The term integrated layer will be used hereinafter to refer to this combination). The inner layer includes a thermoplastic fiber such as one made from polyester, polypropylene, acrylic or nylon fibers or blends or the like and may optionally contain a nonthermoplastic fiber to add absorbent capacity such as rayon, superabsorbent rayon, cellulosic fibers or blends of the fibers enumerated above. The thermoplastic fibers may be crimped to add resiliency to this layer.

DETAILED DESCRIPTION OF THE INVENTION

More specifically, the inner pledget layer is formed of a more highly absorbent material such as compressed fluff. An especially preferred absorbent insert is a surfactant treated thermoplastic microfibrous web. This web has excellent wicking properties and does not collapse when wet.

The outer or transfer layer can be formed in a conventional manner by carding or airlaying or randomized carding.

The outer layer has a basic weight range of 30–400 grams per square meter and the thickness in its uncompressed state, generally between 0.1 to about 1 centimeters.

The web forming the outer layer may contain fibers which are fused to add integrity. Suitable low melting point fusible fibers are Hercules 123, a polypropylene fiber sold by Hercules Fiber Marketing, Norcross, Ga.; VINYON, a vinyl chloride/vinyl acetate copolymer sold by Avtex Fibers, Inc. of New York, N.Y.; Eastman 410 amorphous or crystalline polyester fibers sold by Eastman Chemical Products, Inc., a subsidary of Eastman Kodak Co., Kingsport, Tenn.; or Chisso ES a bicomponent polypropylene/polyethylene fiber sold by Chisso Ltd., Osaka, Japan which due to its differential melting point for each component of the fiber, could be used for purposes of including a fusible component as well as a separate thermoplastic fiber. Fusing to a limited extent will aid in the transfer of menses through the layer, but will also act to diminish resiliency. The level of fusing and whether fusing is desired therefore depends upon the ultimate choice of a final property characteristics for this layer.

The thermoplastic fiber-containing web is then integrated to a thermoplastic cover material. Integration refers to the bonding of the cover at distances not greater than 2 centimeters apart on the surface of the cover. Bonding to accomplish integration can be by the application of heat such as by hot calender embossing or by ultrasonic means, or it can be by mechanical manipulation of fibers with or without heat as in needling. It is preferred that bonding be by heating means and ultrasonic bonding is particularly preferred. The bonding, if by heat may be something less than fusing, such as described in U.S. Pat. No. 3,855,046.

The bonding step may, in fact, produce holes in the cover material itself which may extend into the web layer depending upon the severity of the bonding treatment.

Integration of the cover to the outer pledget layer alters the character of the layer by providing transfer zones of increased density and compression which diminish as they extend radially from the integration sites through the depth of the transfer layer; although it should be noted that the part of the layer directly under the integration site may be entirely fused and not part of this transfer zone.

These zones which are observable and quantifiable by microscopic examination as to their extent and degree of compaction provide conduits for transfer of menses due to the compression and the subsequent smaller capallaries formed in the transfer zone. The layer, in the transfer zone, therefore performs as a conduit to convey fluid into the microfibrous inner layer. There is of course also some retention in the transfer zone area. The remainder of this layer having larger capillaries than the transfer zone does not as readily conduct fluid downward in the z direction.

Directly above these transfer zones are transfer areas which indicate the portion of the cover where the transfer will first occur. These transfer areas vary from being irregular to circular in shape and may overlap. The transfer areas are, however, a surface phenomenon as opposed to a z direction phenomenon as is the case with the zones.

One caution should be observed, however, and that is where integration occurs by fusing. Contiguous integration sites and several closely spaced integration sites are to be avoided because the actual fused area blocks fluid transfer. At least in this instance it is generally preferred to maintain individual integration sites more than 0.15 centimeters apart. Also, it should be noted that integration, particularly by fusing tends to stiffen the composite layer formed and this adversely effects the desirable resilient properties of the integrated combination.

The cover which forms the other part of the integrated composite layer is primarily of a nonwoven thermoplastic web which should be of a sufficiently open structure to enhance the transfer of viscous fluid menses. It is preferred for purposes of this invention that the web be sufficiently open to enhance transfer. While the surface of the cover may be altered with treatment with suitable surface active agents to aid in the transfer, certain cover structures have been found to perform better than others and their performance has been correlated to the numbers of small holes present in the web.

Several cover materials were submitted for examination by a Quantimet 900 Image Analyzer made by Cambridge-Imanco Limited, Cambridge, England. A Bausch & Lomb Model L transmitted light photomicrographic unit was employed to take photomicrographs of cover materials which had been previously tested. The photomicrographs were examined with the Image Analyzer pixel size set at 13.28 microns.

For a cover to be acceptable no more than 40% of the holes may have a breadth of less than 27.3 microns; with preferred covers having less than 25% of the holes which are less than 27.3 microns. Breadth is measured as the maximum dimension of the hole measure at 90° to the major axis of the hole.

A second set of measurements which were taken directly on the cover material with a pixel size of 3.04 microns revealed that preferred cover materials should have no more than 90 holes/mm$^2$ with a breadth of less than 13 microns. Generally, this latter breadth measurement has been correlated to fluid retention within the cover. In other words, a potential cover material may transfer fluid but retain a significant amount with the cover holes, thus producing a wet feeling surface which is generally to be avoided.

A most preferred cover material which meets both criteria is a uniform spunbonded nonwoven web having 3 denier or larger filaments. Such a material is described in U.S. Pat. No. 4,340,563 by Appel and Morman. While other suitable thermoplastic cover materials may also be utilized, the materials particularly preferred as discussed above have the advantage of being more permeable to the larger sized solid components of menses.

The second or inner layer of the composite pledget is formed of a nonwoven hydrophobic thermoplastic filamentary microfibrous web which has been rendered increasingly hydrophilic. The fiber or filament used in this web has an average diameter less than 15 microns and preferably less than 12 microns. If the web used in this invention is formed in discontinuous fashion, i.e., made up of a plurality of fibrels or fibers then fibers of 15 microns or less should make up 50% of the fibers to be suitable for purposes of this invention. The web which is conventionally hydrophobic in nature is rendered less hydrophobic by treatment with a suitable medically safe surfactant examples of which are: sodium alkyl sulfosuccinates; polyoxyethylene alkanols, phenols, and sorbitan esters of $C_{12}$–$C_2O$ fatty acids; alkylammonium alkyl sulfates and mixtures of the above with the anionic and/or nonionic surfactants generally preferred. The wetting agents are present at a level of 0.1 to 5.0% by weight of the fibers preferred with a range of 0.5 to 3.0% especially preferred depending on the wetting agent chosen, while bearing in mind that lower fiber diameter increases capillary attraction, wicking and fluid retention. Of course, excess levels of wetting agents may be used but there is little gain in performance above the 5% level. It is possible to add absorbent capacity by including absorbent particles such as superabsorbents in the web itself.

The microfiber material is further described in pending U.S. application Ser. No. 266,795 which has been informally allowed, and is hereby incorporated by reference.

DESCRIPTION OF DRAWINGS

This invention can best be understood by reference to the drawings in which

As shown in FIG. 1, a flat, rectangular web of the integrated layer is formed and in this instance is made from a web weighing 2.1 grams and formed into an 8.0×4 inch rectangle. The composition of the web is 75% polypropylene fiber and 25% polyester fiber blend integrated with a cover material such as the uniform spunbonded nonwoven web as described in the Morman & Appel patent mentioned earlier was spotbonded as described in U.S. Pat. No. 3,855,046 under 10 grams per square feet pressure forming a pattern of integration sites spaced about 3/16 in. from each other and the nonwoven microfibrous web 11 was positiond on one-half of the rectangular web 10 which was folded along the score line S to completely overlap the microfibrous web as shown in FIG. 2. The microfibrous web 11 as can be seen phantom lines in FIG. 2 is completely surrounded by the integrated composite layer 10 with the integration sites 12 being shown on the external surfaces of the multi-layered composite. The open edge is sealed such as by heat or ultrasonics by fused lines 13 and the removal string is pierced through and looped in the center of this multi-layered batt. The structure is then formed into an inverted cone shape and compressed mostly in a radial dimension to form a pledget approximately 2 inches in length which will fit into a conventional tampon applicator tube for eventual insertion by the wearer. FIG. 3 depicts the tampon after compression with fold lines 15 and withdrawal string 14 shown as the pledget would exist in the tube or after discharge from the tube by the user.

Compression of the formed multi-layered pledget is slight so that the density currently preferred is 0.19 grams per cc as opposed to a conventional cellulosic type tampon having a density of at least 0.4 grams per cc. This reduced density accounts for the increased comfort and resiliency associated with this particular product. Generally, the density of the multilayered pledget is preferred to be between about 0.15 and 0.25 g/cc. Extremely dense microfiber webs are to be avoided because the capillaries may be rendered to small to be effective.

Figure 4:
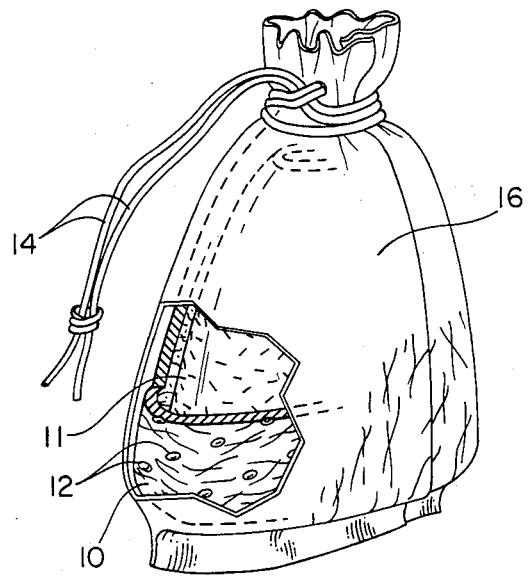

The embodiment in FIG. 4 shows an alternative configuration in which a second cover 16 is placed over the integrated composite 10 and the inner layer of microfibers 11. This second cover 16 can be closed with withdrawal string 14 being looped through the cover and the integrated layer and used to draw the open end together and then the string 14 can be permanently affixed to the second nonwoven cover, e.g., by fusing.

Figure 1:
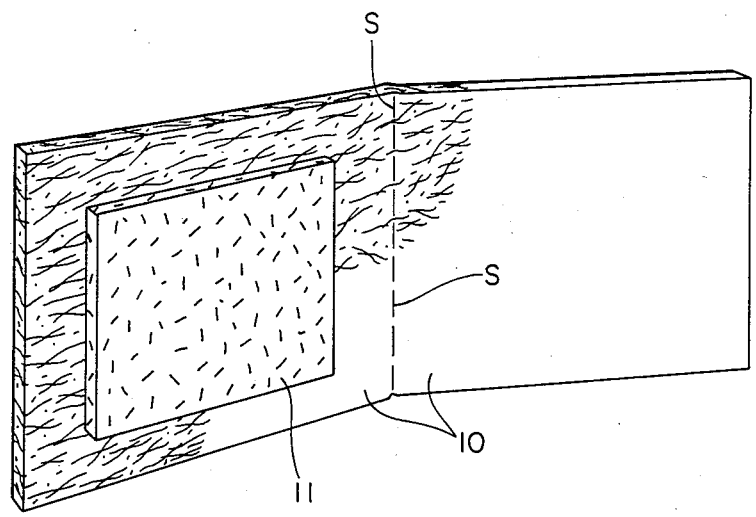
FIGS. 1, 2 and 3 show one example of a preferred embodiment of the subject invention and FIG. 4 relates to a second preferred embodiment.
Figure 2:
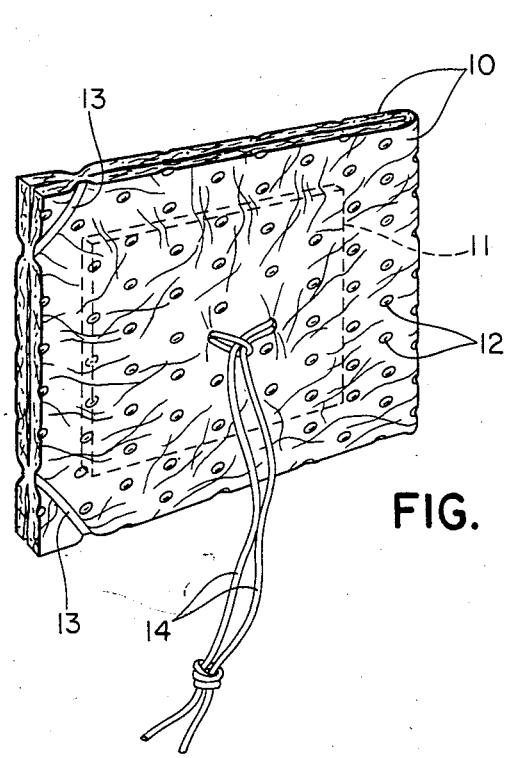
Figure 3:
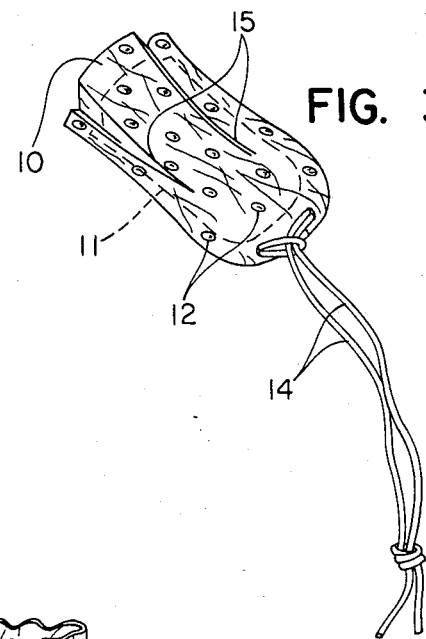

Interestingly, when absorbency tests were run on the composite illustrated in FIGS. 1 through 3 it was determined that the absorbency as calculated on a gram absorbed per gram weight of the absorbent was almost identical to the composite resilient material as it was for the microfiber. In each instance this was approximately 4 grams absorbed per gram weight of absorbent. This is surprising because one would expect that the microfiber web, due to its small capillaries should be a more effective absorbing agent on a gram per gram basis.

Generally the tampon pledget itself weighs about 2.7 gms. and it is preferred that at least 15% of the pledget weight is microfiber. At levels below 15% the pledget acts more like a sponge than a tampon. When the weight percent of the microfiber exceeds 55% there is a noticeable decline on absorbent capacity.

What is claimed is:

1. A tampon comprising in combination; a withdrawal string, a pledget having an inner absorbent layer, and an absorbent outer portion made of a resilient transfer layer containing thermoplastic fibers said transfer layer being integrated to a nonwoven thermoplastic cover overlying the said transfer layer spaced bonding said bonding surrounded by transfer zones for preferentiably conducting fluid.

2. The tampon according to claim 1 wherein the inner absorbent layer is a surfactant treated nonwoven microfiberous web.

3. The tampon according to claim 2 wherein the inner layer includes superabsorbent particles.

4. The tampon according to claim 1 wherein the transfer layer includes cellulosic fibers.

5. The tampon according to claim 1 wherein the density of the pledget is between about 0.15 and 0.25 g/cc.

6. The tampon according to claims 2, 3, 4 or 5 wherein the microfiber is from 15 to 55% by weight of the pledget.

* * * * *